(12) United States Patent
Govari et al.

(10) Patent No.: US 9,687,289 B2
(45) Date of Patent: Jun. 27, 2017

(54) CONTACT ASSESSMENT BASED ON PHASE MEASUREMENT

(75) Inventors: Assaf Govari, Haifa (IL); Andres Claudio Altmann, Haifa (IL); Yaron Ephrath, Karkur (IL)

(73) Assignee: Biosense Webster (Israel) Ltd. (IL)

( * ) Notice: Subject to any disclaimer, the term of this patent is extended or adjusted under 35 U.S.C. 154(b) by 955 days.

(21) Appl. No.: 13/343,024

(22) Filed: Jan. 4, 2012

(65) Prior Publication Data
US 2013/0172875 A1 Jul. 4, 2013

(51) Int. Cl.
*A61B 18/00* (2006.01)
*A61B 18/12* (2006.01)
*A61B 18/14* (2006.01)
*A61B 90/00* (2016.01)

(52) U.S. Cl.
CPC .......... *A61B 18/12* (2013.01); *A61B 18/1492* (2013.01); *A61B 2018/00351* (2013.01); *A61B 2018/00577* (2013.01); *A61B 2018/00642* (2013.01); *A61B 2018/00666* (2013.01); *A61B 2018/00755* (2013.01); *A61B 2018/00869* (2013.01); *A61B 2018/00875* (2013.01); *A61B 2018/1467* (2013.01); *A61B 2090/065* (2016.02)

(58) Field of Classification Search
CPC A61B 2018/00577; A61B 2018/00869; A61B 2018/00351; A61B 2018/00642; A61B 2018/00755; A61B 2018/0075; A61B 18/1492; A61B 18/12
See application file for complete search history.

(56) References Cited

U.S. PATENT DOCUMENTS

| | | | |
|---|---|---|---|
| 3,841,150 | A | 10/1974 | Pearson |
| 3,971,364 | A | 7/1976 | Fletcher et al. |
| 4,764,114 | A | 8/1988 | Jeffcoat et al. |
| 4,856,993 | A | 8/1989 | Maness et al. |

(Continued)

FOREIGN PATENT DOCUMENTS

| | | |
|---|---|---|
| DE | 19750441 A | 6/1999 |
| EP | 928601 A1 | 7/1999 |

(Continued)

OTHER PUBLICATIONS

Biter, William J. et al., "Magnetic Wire Strain Sensor", 33rd International Sampe Technical Conference, Nov. 5-8, 2001, vol. 33, pp. 12-23, Seattle, WA.

(Continued)

*Primary Examiner* — William Levicky (57) ABSTRACT

Methods and systems achieve tissue ablation, which is carried out by inserting a probe having an ablation electrode into a body of a living subject, and while the ablation electrode is in a non-contacting relationship to a target tissue, making a pre-contact determination of a phase of an electrical current passing between the ablation electrode and another electrode. The ablation electrode is placed in contact with the target tissue, and while the ablation electrode is in the contacting relationship, a dosage of energy is applied via the ablation electrode to the target tissue for ablation thereof. Iterative intra-operative determinations of the phase of the electrical current are made. When one of the intra-operative determinations satisfies a termination criterion, the energy application is terminated.

9 Claims, 3 Drawing Sheets

(56) References Cited

U.S. PATENT DOCUMENTS

| | | |
|---|---|---|
| 4,930,494 A | 6/1990 | Takehana et al. |
| 5,263,493 A | 11/1993 | Avitall |
| 5,368,564 A | 11/1994 | Savage |
| 5,391,199 A | 2/1995 | Ben-Haim |
| 5,452,719 A | 9/1995 | Eisman et al. |
| 5,462,527 A | 10/1995 | Stevens-Wright et al. |
| 5,487,757 A | 1/1996 | Truckai et al. |
| 5,499,542 A | 3/1996 | Morlan |
| 5,542,434 A | 8/1996 | Imran et al. |
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,728,149 A | 3/1998 | Laske et al. |
| 5,769,843 A | 6/1998 | Abela et al. |
| 5,826,576 A | 10/1998 | West |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,865,801 A | 2/1999 | Houser |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,036,654 A | 3/2000 | Quinn et al. |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,266,551 B1 | 7/2001 | Osadchy et al. |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy et al. |
| 6,351,549 B1 | 2/2002 | Souluer |
| 6,398,738 B1 | 6/2002 | Millar |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,569,098 B2 | 5/2003 | Kawchuk |
| 6,574,492 B1 | 6/2003 | Ben Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben Haim et al. |
| 6,695,808 B2 | 2/2004 | Tom |
| 6,711,429 B1 | 3/2004 | Gilboa et al. |
| 6,727,371 B2 | 4/2004 | ***Walch et al. |
| 6,814,733 B2 | 11/2004 | Schwartz et al. |
| 6,835,173 B2 | 12/2004 | Couvillon, Jr. |
| 6,892,091 B1 | 5/2005 | Ben Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,003,342 B2 | 2/2006 | Plaza |
| 7,052,493 B2* | 5/2006 | Vaska ............... A61N 7/02 606/41 |
| 7,077,823 B2 | 7/2006 | McDaniel |
| 7,156,816 B2 | 1/2007 | Schwartz et al. |
| 7,235,070 B2 | 6/2007 | Vanney |
| 7,297,116 B2 | 11/2007 | Varghese et al. |
| 7,306,593 B2 | 12/2007 | Keidar et al. |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari et al. |
| 7,604,605 B2 | 10/2009 | Zvuloni |
| 7,662,151 B2 | 2/2010 | Crompton, Jr. et al. |
| 7,681,432 B2 | 3/2010 | Hay et al. |
| 7,686,767 B2 | 3/2010 | Maschke |
| 7,911,315 B2 | 3/2011 | Bradley |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,265,745 B2 | 9/2012 | Hauck et al. |
| 8,357,152 B2 | 1/2013 | Govari et al. |
| 8,374,819 B2 | 2/2013 | Govari et al. |
| 8,535,308 B2 | 9/2013 | Govari et al. |
| 8,900,229 B2 | 12/2014 | Govari et al. |
| 8,926,528 B2 | 1/2015 | Govari et al. |
| 9,033,916 B2 | 5/2015 | Schultz |
| 9,265,913 B2 | 2/2016 | Fallin et al. |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0065455 A1 | 5/2002 | Ben Haim et al. |
| 2002/0068866 A1 | 6/2002 | Zikorus et al. |
| 2002/0068931 A1 | 6/2002 | Wong et al. |
| 2002/0087089 A1 | 7/2002 | Ben-Haim |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0043649 A1 | 2/2005 | Urie |
| 2005/0080429 A1 | 4/2005 | Freyman et al. |
| 2005/0096590 A1 | 5/2005 | Gullickson et al. |
| 2005/0148903 A1 | 7/2005 | Diamantopoulos |
| 2005/0171569 A1 | 8/2005 | Girard et al. |
| 2005/0228274 A1 | 10/2005 | Boese et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0064038 A1 | 3/2006 | Omata et al. |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo et al. |
| 2006/0241366 A1 | 10/2006 | Falwell et al. |
| 2006/0247618 A1 | 11/2006 | Kaplan et al. |
| 2006/0276703 A1 | 12/2006 | Fuimaono et al. |
| 2007/0021742 A1 | 1/2007 | Viswanathan |
| 2007/0060832 A1 | 3/2007 | Levin |
| 2007/0060847 A1 | 3/2007 | Leo et al. |

(56) References Cited

U.S. PATENT DOCUMENTS

| | | |
|---|---|---|
| 2007/0083193 A1 | 4/2007 | Werneth et al. |
| 2007/0100332 A1 | 5/2007 | Paul et al. |
| 2007/0106114 A1 | 5/2007 | Sugimoto et al. |
| 2007/0106165 A1 | 5/2007 | Tulkki et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167804 A1 | 7/2007 | Park |
| 2007/0167818 A1 | 7/2007 | Osborn et al. |
| 2007/0167819 A1 | 7/2007 | Osborn et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0233044 A1 | 10/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0161796 A1 | 7/2008 | Cao et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsummura |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2008/0312521 A1* | 12/2008 | Solomon ............... A61B 5/053 600/374 |
| 2009/0010021 A1 | 1/2009 | Smith et al. |
| 2009/0062642 A1 | 3/2009 | Hauck |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306521 A1 | 12/2009 | Ermakov et al. |
| 2009/0306650 A1 | 12/2009 | Govari et al. |
| 2009/0318798 A1 | 12/2009 | Singh et al. |
| 2010/0036285 A1 | 2/2010 | Govari et al. |
| 2010/0063478 A1 | 3/2010 | Selkee |
| 2010/0069921 A1* | 3/2010 | Miller ............... A61B 18/1233 606/130 |
| 2010/0121138 A1 | 5/2010 | Goldenberg et al. |
| 2010/0121214 A1 | 5/2010 | Giftakis et al. |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0222668 A1 | 9/2010 | Dalke et al. |
| 2010/0262001 A1 | 10/2010 | Morris et al. |
| 2010/0274239 A1* | 10/2010 | Paul ............... A61B 18/1206 606/33 |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0152880 A1 | 6/2011 | Alvarez et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 8266486 A | 10/1996 |
| JP | 2000126301 A | 5/2000 |
| JP | 2000508224 A | 7/2000 |
| JP | 2005040215 | 2/2005 |
| JP | 2005040215 A | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| JP | 2010-514504 | 5/2010 |
| WO | WO 94/17856 A1 | 8/1994 |
| WO | WO 95/10326 A | 4/1995 |
| WO | WO 96/05768 A | 2/1996 |
| WO | WO 97/29678 | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/029563 | 3/2006 |
| WO | WO 2006/043884 A1 | 4/2006 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 A | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |

(56) References Cited

FOREIGN PATENT DOCUMENTS

| WO | WO 2009/078280 A | 6/2009 |
|---|---|---|
| WO | WO 2009/085470 A | 7/2009 |
| WO | WO 2009/147399 A1 | 12/2009 |
| WO | WO 2010/008975 A | 1/2010 |
| WO | WO 2011/046874 A1 | 4/2011 |

OTHER PUBLICATIONS

Biter, William J. et al., "Magnetic Wire for Monitoring Strain in Composites", *Sensors*, Jun. 2001, www.sensormag.com, pp. 110-114.
Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.
Instron Marketing Brochure, "Medical Device Testing Systems", Instron 2007 http://_/web.archive.org/web/20080318092822/http://_/www.instron.com.tr/wa/library/streamfile.aspx?doc=1678&downland=true.
Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).
Okumura, M.D. Yasuo et al. "A Systematic Analysis of In Vivo Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.
Peirs, J. et al., "Design of an Optical Force Sensor for Force Feedback during Minimally Invasive Robotic Surgery", Eurosensors XVII, 2003, pp. 1063-1066, http://_/mech.kuleuven.be/micro/pub/medic/Paper_Eurosensors_2003_MIS_sensor.extended.pdf.
Partial European Search Report mailed on Sep. 18, 2009 from related European Patent Application No. 08253265.6.
Partial European Search Report mailed on Dec. 7, 2009 from related European Patent Application No. 09251502.2.
European Search Report mailed on Mar. 8, 2010 from related European Patent Application No. 09252143.4.
Partial European Search Report mailed on Mar. 29, 2010 from related European Patent Application No. 09252879.3.
Partial European Search Report mailed on Apr. 1, 2010 from related European Patent Application No. 09252721.7.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from corresponding European Patent Application No. 13150145.4.
European Search Report mailed on Feb. 15, 2012 from corresponding European Patent Application No. 11182854.7.
European Search Report mailed on Apr. 9, 2013 from related European Patent Application No. 13150145.4.
Instron, "Series 3300 Load Frames, Reference Manual Equipment", Instron, pp. 1-5 and 1-10, 2004.

* cited by examiner

CONTACT ASSESSMENT BASED ON PHASE MEASUREMENT

BACKGROUND OF THE INVENTION

Field of the Invention

This invention relates to tissue ablation systems. More particularly, this invention relates to monitoring of contact between an invasive probe and tissue within the body.

Description of the Related Art

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to cease or modify the propagation of unwanted electrical signals from one portion of the heart to another. The ablation process destroys the unwanted electrical pathways by formation of non-conducting lesions.

Verification of physical electrode contact with the target tissue is important for controlling the delivery of ablation energy. Attempts in the art to verify electrode contact with the tissue have been extensive, and various techniques have been suggested. For example, U.S. Pat. No. 6,695,808 describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724 describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332 describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

U.S. Pat. No. 7,306,593, issued to Keidar et al., describes a method for ablating tissue in an organ by contacting a probe inside the body with the tissue to be ablated, and measuring one or more local parameters at the position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact indication may be unreliable, however, and is sensitive to changes in the impedance between the body-surface electrode and the skin.

U.S. Patent Application Publication Nos. 2008/0288038 and 2008/0275465, all by Sauarav et al., which are herein incorporated by reference, describe an electrode catheter system may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

SUMMARY OF THE INVENTION

There is provided according to embodiments of the invention a method of ablation, which is carried out by inserting a probe having an ablation electrode into a body of a living subject, and while the ablation electrode is in a non-contacting relationship to a target tissue, making a pre-contact determination of a phase of an electrical current passing between the ablation electrode and another electrode. The method is further carried out by urging the ablation electrode into a contacting relationship with the target tissue, and while the ablation electrode is in the contacting relationship applying a dosage of energy via the ablation electrode to the target tissue for ablation thereof, iteratively making intra-operative determinations of the phase of the electrical current. The method is further carried out by establishing that one of the intra-operative determinations satisfies a termination criterion for completion of the ablation, and responsively thereto, terminating the energy application.

One aspect of the method includes displaying a visual indication of the intra-operative determinations of the phase of the electrical current. The visual indication may include a progress display of the ablation with respect to an intended lesion in the target tissue.

According to yet another aspect of the method, the termination criterion includes a difference between one of the intra-operative determinations and the pre-contact determination that is less than a predetermined value.

According to still another aspect of the method, the termination criterion includes a failure of one of the intra-operative determinations to vary from a preceding one of the intra-operative determinations by more than a threshold value.

According to an additional aspect of the method, making the pre-contact determination and the intra-operative determinations comprise measuring a phase of an impedance between an electrode on the probe and a body-surface electrode.

According to one aspect of the method, making the pre-contact determination and the intra-operative determinations includes making a comparison with respective phases of a reference waveform taken from a reference electrode that is spaced apart from the target tissue.

In a further aspect of the method, making intra-operative determinations is performed every 2-5 seconds.

In yet another aspect of the method, making intra-operative determinations and applying a dosage of energy are performed concurrently.

According to still another aspect of the method, making a pre-contact determination is performed at a power of less than 10 milliwatts.

According to an additional aspect of the method, making intra-operative determinations is performed at a power of 5-50 watts.

Other embodiments of the invention provide apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Figure 1:
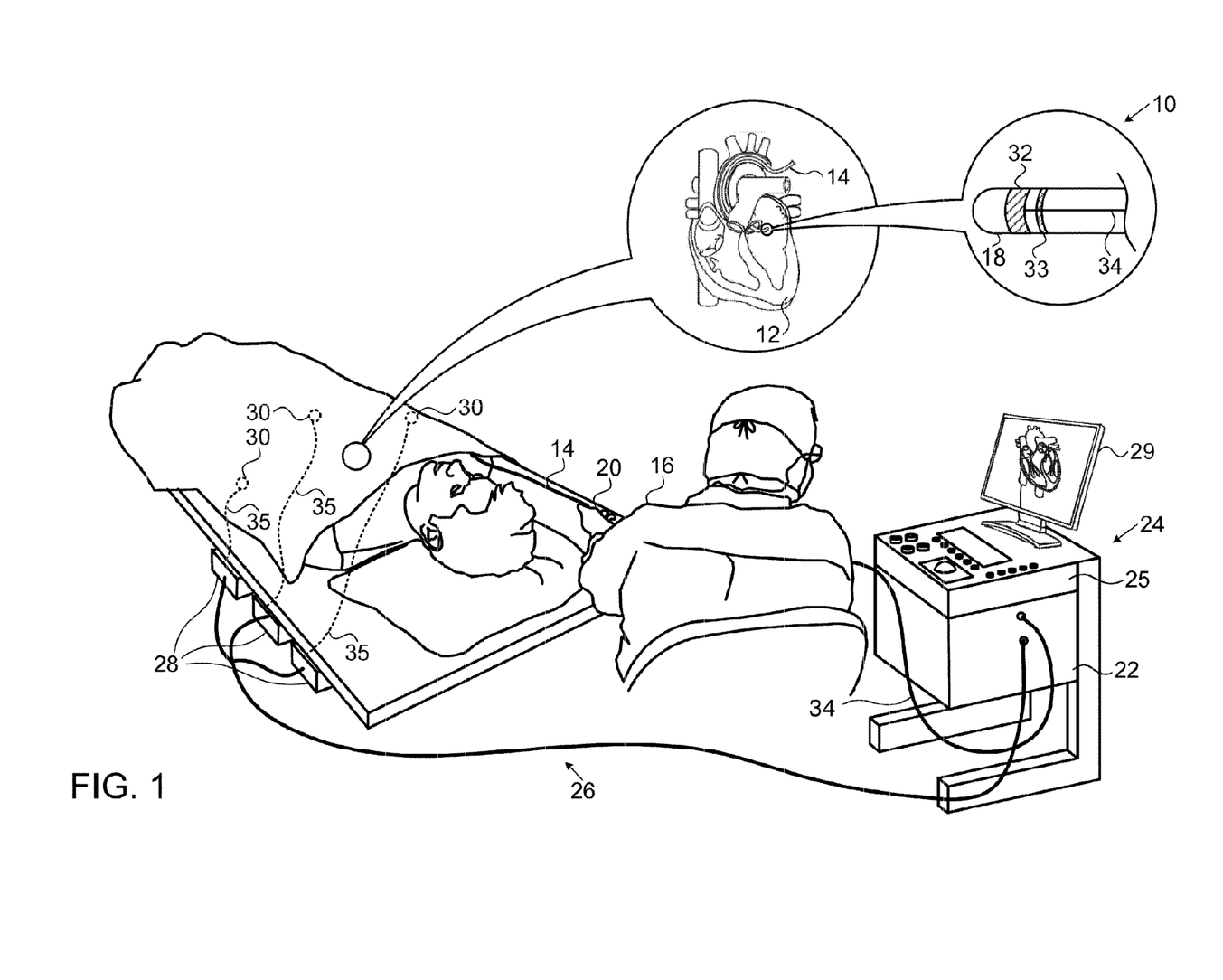
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning system 26 of the system 10 that measures location and orientation coordinates of the catheter 14.

In one embodiment, the positioning system 26 comprises a magnetic position tracking arrangement that determines the position and orientation of the catheter 14 by generating magnetic fields in a predefined working volume its vicinity and sensing these fields at the catheter using field generating coils 28 and may include impedance measurement, as taught, for example in U.S. Patent Application Publication No. 2007/0060832, which is herein incorporated by reference. The positioning system 26 may be enhanced by position measurements using the impedance measurements described in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system 26 to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Embodiments of the present invention measure the phase of the impedance between the catheter electrode and the body-surface electrode. This phase shifts markedly with distance between the catheter electrode and the tissue over the range of about 1-2 mm, between contact and non-contact, due to the attendant change in the capacitance between the electrode and the tissue. It thus provides a sensitive measure of short-range distance and contact.

Figure 2:
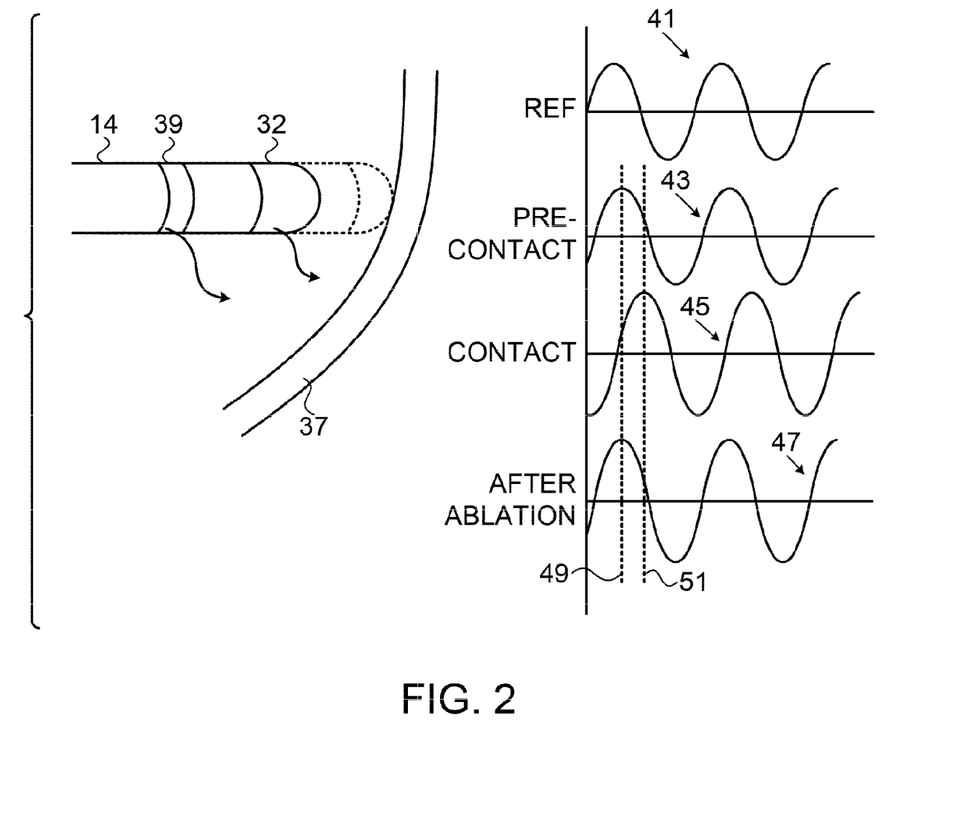
FIG. 2 is a composite drawing illustrating phase relationships of currents passing through an electrode of the catheter as it moves into contact with heart tissue in accordance with an embodiment of the invention.

Reference is now made to FIG. 2, which is a composite drawing illustrating phase relationships of currents passing through an electrode of the catheter 14 as it moves into contact with wall 37 of heart 12 (FIG. 1) in accordance with an embodiment of the invention. A reference electrode 39 is optionally provided for this purpose. The reference electrode 39 does not contact the wall 37. The electrodes are driven with a signal at a known frequency, which passes through the tissue and is received by the body surface electrodes 30 (FIG. 1) or some other receiving electrode. Waveforms at the right side of FIG. 2 include, from top to bottom, a reference waveform 41 taken from the reference electrode 39, a pre-contact waveform 43 from the ablation electrode 32, taken when the ablation electrode 32 is out of contact with the wall 37, a contact waveform 45, taken when the ablation electrode 32 is in mechanical contact with the wall 37, and a post-ablation waveform 47, following completion of ablative therapy but while the ablation electrode 32 is still in contact with the wall 37.

Phase shifts are indicated by displacement of vertical lines 49, 51 drawn through corresponding maxima of the pre-contact waveform 43 and the contact waveform 45. The phase shifts occur when the ablation electrode 32 is brought into contact with the wall 37. The inventors have discovered that phase measurement of this sort can be used not only to verify tissue contact, but also to check the progress of ablation: as the lesion is created and while the ablation electrode 32 maintains contact with the tissue, the phase of the impedance between the ablation electrode 32 and the tissue changes. Alternatively, the change in the phase between the ablation electrode 32 and the tissue can be determined by any of the other phase determination methods described in the above mentioned U.S. Patent Application Publication Nos. 2008/0288038 and 2008/0275465. The appearance of a waveform approximating post-ablation waveform 47 gives an indication that the tissue has been ablated.

During the ablation, persistent contact between the ablation electrode 32 and the wall 37 may be confirmed using a position sensor in conjunction with the positioning processor 22 (FIG. 1), or by any of the other techniques described above for verifying physical electrode contact with the target tissue.

It should be noted that the phase of the signal received from the reference electrode 39 does not change substantially as the tip electrode makes contact with the tissue. The reference electrode 39 may therefore be used as a basis for measuring the phase shift of the current passing through the ablation electrode 32 or another tip electrode (not shown). The ablator can operate while concurrently monitoring the phase shift. It is not necessary to interlace the two operations.

Figure 3:
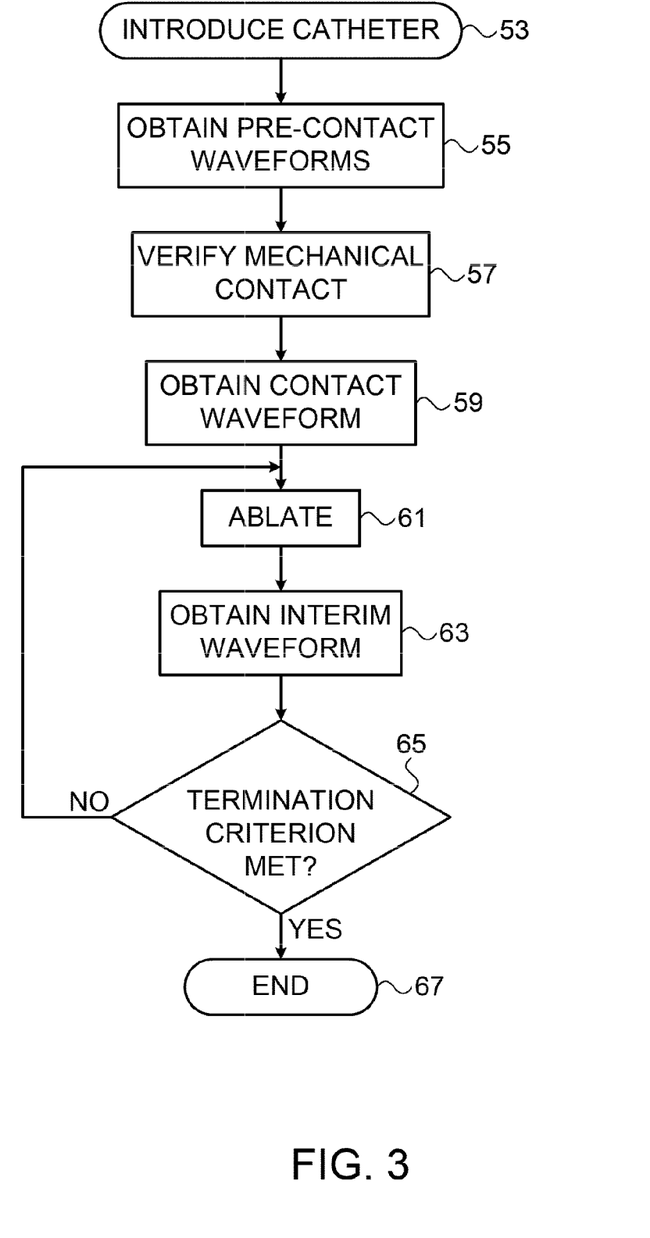
FIG. 3 is a flow chart of a method of tissue ablation in accordance with an embodiment of the invention.

Reference is now made to FIG. 3, which is a flow chart of a method of tissue ablation in accordance with an embodiment of the invention. At initial step 53 a catheter, constructed in accordance with one of the above-described embodiments, is introduced into the heart, and an ablation electrode, together with its associated temperature sensor, positioned near a target site using the positioning system 26 (FIG. 1).

Next, at step 55 a reading is taken to obtain the phase of a pre-contact waveform. This may be done by operating the ablation electrode 32 (FIG. 2) in a calibration mode. Optionally, the phase of the pre-contact waveform is related to a waveform read from a reference electrode. In either case, the results are memorized.

Next at step 57, mechanical contact between the ablation electrode 32 and the wall 37 is verified, using any of the aforementioned methods.

Next, at step 59 a baseline contact waveform is obtained and memorized.

Next, at step 61, the ablation electrode is activated to ablate the target tissue.

Next, at step 63, after an interval that may vary according to the lesion desired and the judgment of the operator, an intra-operative waveform is obtained and its phase angle with respect to the baseline contact waveform or the reference waveform ascertained. The phase angle of the intra-operative waveform and a calculated estimation of the degree of completion of the intended lesion may be displayed for the operator. When the rate of change of the phase angle approaches zero, it may be inferred that changes in the tissue are no longer occurring and that the ablation is essentially complete.

Typically, the phase angle is determined every few seconds, e.g., every 2-5, seconds, depending on the stability of the measurement.

The power requirement for obtaining phase angle readings is a less than 10 milliwatts if the ablator is idle. If the ablator is active then 5-50 watts is required.

Control now proceeds to decision step 65, where it is determined if a termination criterion has been met. Termination criteria that may apply are, for example:

(1) an absence of change in the phase angle over a time interval;

(2) a return of the phase angle of the intra-operative waveform to that of the pre-contact waveform; and (3) failure of the phase angle to shift more than a threshold amount, e.g., 50% in comparison to an intra-operative waveform obtained in a previous iteration of a loop including steps 61, 63.

If a termination criterion has not been met at decision step 65, then control returns to step 61. Otherwise control proceeds to final step 67, where the procedure is terminated.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of ablation using a body-surface electrode and a probe, comprising the steps of:

inserting the probe into a body of a living subject, the probe having a proximal end and a distal end terminating in a distal tip, with an ablation electrode affixed to the distal tip, and a reference electrode affixed along the distal end proximal to the ablation electrode;

passing a current at a known frequency between the reference electrode and the body-surface electrode and reading a reference waveform having a reference phase from the reference electrode;

while the ablation electrode is in a non-contacting relationship to a target tissue, passing the current at the known frequency between the ablation electrode and the body-surface electrode and reading a non-contact waveform having a non-contact phase from the ablation electrode;

making a pre-contact determination by comparing the reference phase to the non-contact phase;

urging the ablation electrode into a contacting relationship with the target tissue;

while the ablation electrode is in the contacting relationship applying a dosage of energy via the ablation electrode to the target tissue for ablation thereof;

while the ablation electrode is in the contacting relationship with target tissue, iteratively passing the current at the known frequency between the ablation electrode and the body-surface electrode and intra-operatively reading a contact waveform having a contact phase from the ablation electrode;

iteratively making intra-operative determinations by comparing the contact phase to the reference phase; and establishing that one of the intra-operative determinations satisfies a termination criterion for completion of the ablation, and responsively thereto, terminating the step of applying a dosage of energy.

2. The method according to claim 1, further comprising the steps of displaying a visual indication of the intra-operative determinations of the phase of the electrical current.

3. The method according to claim 2, wherein the visual indication comprises a progress of the ablation with respect to an intended lesion in the target tissue.

4. The method according to claim 2, wherein the termination criterion comprises a difference between one of the intra-operative determinations and the pre-contact determination that is less than a predetermined value.

5. The method according to claim 2, wherein the termination criterion comprises a failure of one of the intra-operative determinations to vary from a preceding one of the intra-operative determinations by more than a threshold value.

6. The method according to claim 1, wherein the step of making intra-operative determinations is performed every 2-5 seconds.

7. The method according to claim 1, wherein the steps of making intra-operative determinations and applying the dosage of energy are performed concurrently.

8. The method according to claim 1, wherein making a pre-contact determination is performed at a power of less than 10 milliwatts.

9. The method according to claim 1, wherein making intra-operative determinations is performed at a power of 5-50 watts.

* * * * *